(12) United States Patent
Coffee et al.

(10) Patent No.: US 7,972,622 B1
(45) Date of Patent: Jul. 5, 2011

(54) METHOD AND APPARATUS FOR MANUFACTURING DISSOLVABLE TABLETS

(75) Inventors: Ronald Alan Coffee, Haslemere (GB); Alastair Bruce Pirrie, Oxford (GB); David Neville Davies, Oxford (GB)

(73) Assignee: Battelle (Memorial Institute), Columbus, OH (US)

( * ) Notice: Subject to any disclaimer, the term of this patent is extended or adjusted under 35 U.S.C. 154(b) by 0 days.

(21) Appl. No.: 10/018,160

(22) PCT Filed: May 5, 2000

(86) PCT No.: PCT/GB00/01728
§ 371 (c)(1),
(2), (4) Date: Nov. 1, 2001

(87) PCT Pub. No.: WO00/67694
PCT Pub. Date: Nov. 16, 2000

(30) Foreign Application Priority Data

May 6, 1999 (GB) .................................. 9910505.8

(51) Int. Cl.
*A61K 9/20* (2006.01)
*A61K 9/64* (2006.01)
(52) U.S. Cl. .......................... 424/465; 424/434; 424/464
(58) Field of Classification Search .................. 424/400, 424/464, 456, 480, 520, 434; 425/6, 174.6; 525/326.9, 386; 528/367, 486
See application file for complete search history.

(56) References Cited

U.S. PATENT DOCUMENTS

| | | | |
|---|---|---|---|
| 4,043,331 A | 8/1977 | Martin et al. | |
| 4,044,404 A | 8/1977 | Martin et al. | |
| 4,197,289 A * | 4/1980 | Sturzenegger et al. | 424/21 |
| 4,704,436 A * | 11/1987 | Barabas | 525/326.9 |
| 4,855,326 A | 8/1989 | Fuisz | |
| 4,878,908 A | 11/1989 | Martin et al. | |
| 4,946,684 A | 8/1990 | Blank et al. | |
| 5,024,671 A | 6/1991 | Tu et al. | |
| 5,215,755 A * | 6/1993 | Roche et al. | 424/480 |
| 5,229,164 A | 7/1993 | Pins | |
| 5,298,261 A | 3/1994 | Pebley et al. | |
| 5,311,884 A | 5/1994 | Scopelianos | |
| 5,320,855 A * | 6/1994 | Roche et al. | 424/495 |
| 5,322,698 A * | 6/1994 | Kovacs et al. | 424/480 |
| 5,376,116 A | 12/1994 | Polar | |
| 5,466,464 A | 11/1995 | Masaki et al. | |
| 5,501,861 A | 3/1996 | Makino et al. | |
| 5,522,879 A | 6/1996 | Scopelianos | |
| 5,567,439 A | 10/1996 | Myers et al. | |
| 5,575,818 A | 11/1996 | Pinchuk | |
| 5,632,772 A | 5/1997 | Alcime et al. | |
| 5,639,278 A | 6/1997 | Dereume et al. | |
| 5,724,004 A | 3/1998 | Reif et al. | |
| 5,736,152 A | 4/1998 | Dunn | |
| 5,762,961 A | 6/1998 | Roser et al. | |
| 5,866,163 A | 2/1999 | Myers et al. | |
| 5,869,098 A | 2/1999 | Misra et al. | |
| 5,980,941 A | 11/1999 | Raiden et al. | |
| 6,074,688 A | 6/2000 | Pletcher et al. | |
| 6,423,346 B1 * | 7/2002 | Hansen et al. | 424/520 |
| 6,465,009 B1 * | 10/2002 | Liu et al. | 424/464 |
| 6,709,669 B1 * | 3/2004 | Murray et al. | 424/434 |

FOREIGN PATENT DOCUMENTS

| | | |
|---|---|---|
| EP | 0 019 929 A | 12/1980 |
| EP | 0542514 A1 | 5/1993 |
| FR | 2 335 206 A | 7/1977 |
| WO | WO 90 06969 A | 6/1990 |
| WO | WO 98/03267 * | 1/1998 |
| WO | WO 98 03267 A | 1/1998 |
| WO | WO 01/54667 A1 | 1/2001 |

OTHER PUBLICATIONS

Bhowmik, D. et al., "Fast Dissolving Tablet: An Overview," Journal of Chemical and Pharmaceutical Research, vol. 1(1) (2009) pp. 163-177.
"Guidance for Industry—Waiver of In Vivo Bioavailability and Bioequivalence Studies for Immediate Release Solid Oral Dosage Forms Containing Certain Active Moieties/Active Ingredients Based on a Biopharmaceutics Classification System," U.S. Department of Health and Human Services, Food and Drug Administration (Jan. 1999) pp. 1-14.
Porter, S. C., "Novel Drug Delivery: Review of Recent Trends with Oral Solid Dosage Forms," American Pharmaceutical Review, pp. 28-35.
Seager, H., "Drug-delivery Products and the Zydis Fast-dissolving Dosage Form," J. Pharm. Pharmacol., vol. 50 (1998) pp. 375-382.
Supervía, A., et al., "Piroxicam fast-dissolving dosage form vs diclofenac sodium in the treatment of acute renal colic: a double-blind controlled trial," British Journal of Urology, vol. 81 (1998) pp. 27-30.

* cited by examiner

*Primary Examiner* — Michael G Hartley
*Assistant Examiner* — Jagadishwar R Samala
(74) *Attorney, Agent, or Firm* — Frost Brown Todd LLC (57) ABSTRACT

Consumable or dissolvable tablets are manufactured by supplying a liquid containing a biodissolvable carrier to an outlet; establishing an electric field between the outlet and a support surface to cause liquid issuing from the outlet to form at least one fiber or fibrils of the biodissolvable carrier which fiber or fibrils deposit(s) onto the surface to form a fiber web or mat; separating the web or mat into a plurality of individual tablets; and incorporating at least one active ingredient on or in the tablets.

11 Claims, 8 Drawing Sheets

METHOD AND APPARATUS FOR MANUFACTURING DISSOLVABLE TABLETS

This invention relates to a method and apparatus for manufacturing dissolvable tablets especially, but not exclusively, dissolvable tablets carrying at least one pharmacologically or biologically active ingredient for therapeutic or prophylactic treatment of an animal such as a human being.

Conventional medicines to be ingested in a solid form are manufactured as a compressed solid tablet or a capsule containing granules which when swallowed enter into the blood stream via the gastro-intestinal tract. Some patients have, however, difficulty in swallowing tablets or capsules. To address this problem and/or to cause the active ingredient to dissolve at the oral mucosa so that it enters the blood stream without entering the gastro intestinal tract, tablets or pills that dissolve on the tongue or in the mouth have been manufactured. This enables buccal delivery of drugs which is especially advantageous where the drug is intended to be delivered to the central nervous system because it enables rapid delivery of the drug to the brain and avoids or at least inhibits delivery of the drug to the non-targeted areas such as the gastrointestinal tract where the presence of the drug may have disadvantageous side effects. Also, drug absorption through the blood-rich epithelium in the mouth, rather than the chemically hostile environment of the stomach and the intestine may generally be advantageous.

Such quick dissolving tablets are conventionally formed by dissolving food or pharmacological grade gelatin to form a gelatin solution. The gelatin solution is then frozen solid converting the water content into ice. The unbound ice is then removed under conditions of low pressure which cause the ice crystals to sublime, turning them directly into water vapour which is collected by a water vapour condenser. The vacuum encourages the orderly migration of water vapour to the condenser and so as to assure that the pressure of the water vapour remains below its triple point as is required for sublimation to occur. Secondary drying is then required to remove the tightly bound (sorbed) water that is strongly attached to the protein molecules. This tightly bound water is difficult to remove because it has a lower vapour pressure than free liquid at the same temperature. Accordingly this secondary drying is a slow process.

The initial rigid ice matrix of the frozen sample and the exceptionally gentle drying ensure that the dried resulting product maintains its structural integrity.

The above described process results in tablets or pills that regularly dissolve or disintegrate in the mouth or on the tongue. However, the process described above is a relatively complex process and generally has to be carried out as a batch-by-batch process.

It is the aim of the present invention to provide apparatus for and a method of manufacturing dissolvable tablets that may dissolve or disintegrate rapidly in the mouth, on the tongue or on any wet surface or in a wet environment, suitable for continuous mass production.

In one aspect, the present invention provides a method of manufacturing dissolvable tablets which comprises using electrohydrodynamic comminution to form a plurality of individual tablets or pills, with each tablet consisting of a fibre web or mat which will dissolve or disintegrate on the tongue or in the mouth of a consumer such as a patient.

The tablets or pills may carry an active ingredient which may be, for example, a drug or other therapeutic agent. The active ingredient may be: carried by (for example in solution with) the liquid or molten material used to form the fibres; provided by electrostatically coating the mat or individual tablets or pills with charged particles; provided by providing the fibres as cored fibres with the core containing the active ingredient; or provided by spraying the fibres after or during deposition with oppositely charged particles of the active ingredient so as to form alternate layers of fibres and the active ingredient. One or more of these techniques may be used to form a particular tablet and different active ingredients may be incorporated into the same tablet. For example, where the tablets are formed by a sandwich of alternate layers of fibres and the active ingredient, the composition of the different layers of active ingredients may be different. In addition, the composition of the fibres forming each of the layers of fibres may be different. This would allow, for example, controlled release of different active ingredients enabling, for example, buccal delivery of a first active ingredient and then later delivery in the gastro-intestinal tract of the same or a different active ingredient, so enabling, for example, sustained or controlled delivery of a drug or other active ingredient or controlled multiple drug therapy.

A method embodying the invention should enable accurate doses of an active ingredient such as a drug to be delivered to any wet surface in a form which is easy and convenient to handle, for example: the application of a growth factor or other compound to an open wound where a pad or tablet would quickly dissolve and release an even distribution of an active ingredient to the surface of the wound; or the delivery of a local anaesthetic to an eye ball after surgery; or delivery of drugs to any animal; or even reconstitution of a dried drug for dissolution in water such as for injection, drinking or eating with food.

The fibres may be formed using any suitable biologically acceptable or compatible polymer that is hydrophilic so that, on contact with a wet surface, it effectively deliquesces becoming liquid by absorbing the water, thereby dissolving. Suitable such polymers include food grade gelatins, polyvinyl pyridine, polyvinyl alcohol, polysucrose, other polysaccharides such as starch and cellulose and its derivatives, sugars and confectionary mixtures such as toffee and caramel and any other biologically compatible products that can be formulated into a liquid solution suitable for use in the electrohydrodynamic comminution process or can be made liquid by the application of heat.

Embodiments of the present invention will now be described, by way of example, with reference to the accompanying drawings in which.

Figure 1:
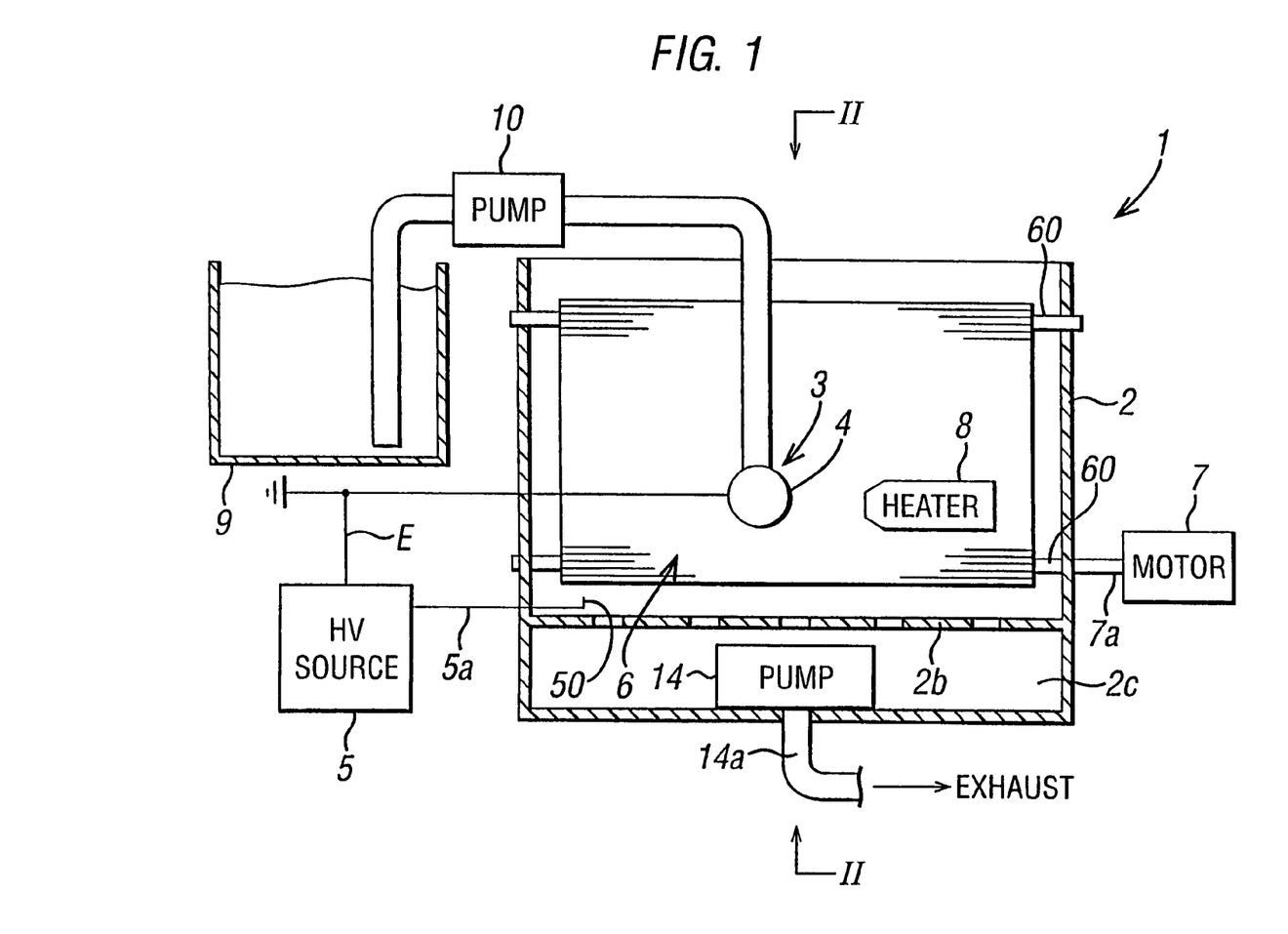
FIG. 1 shows a part sectional very schematic side view of apparatus embodying the invention.

Referring now to the drawings, the apparatus 1 shown in FIG. 1 consists of a container 2 made of thermally insulative material such as a glass, or a plastics material such as Perspex (trade mark).

A comminution arrangement 3 is mounted within the chamber 2. The comminution arrangement 3 comprises a hollow tube 4 having an outlet nozzle 4'. The tube 4 is electrically conductive at least adjacent its nozzle 4'. The electrically conductive nozzle 4' is coupled to the earth terminal E of a high voltage source or supply 5 mounted outside the chamber 2. The high voltage terminal 5a of the high voltage supply 5 is coupled to a corona discharge electrode 50 for charging a support surface 6 disposed opposite the outlet nozzle 4a so as to enable an electric field to be established between the nozzle 4a and the support surface 6. Other ways of charging the support surface 6 such as a brush contact may be used, but the use of a corona discharge electrode 50 has the advantage of avoiding arcing and subsequent erosion.

Figure 2:
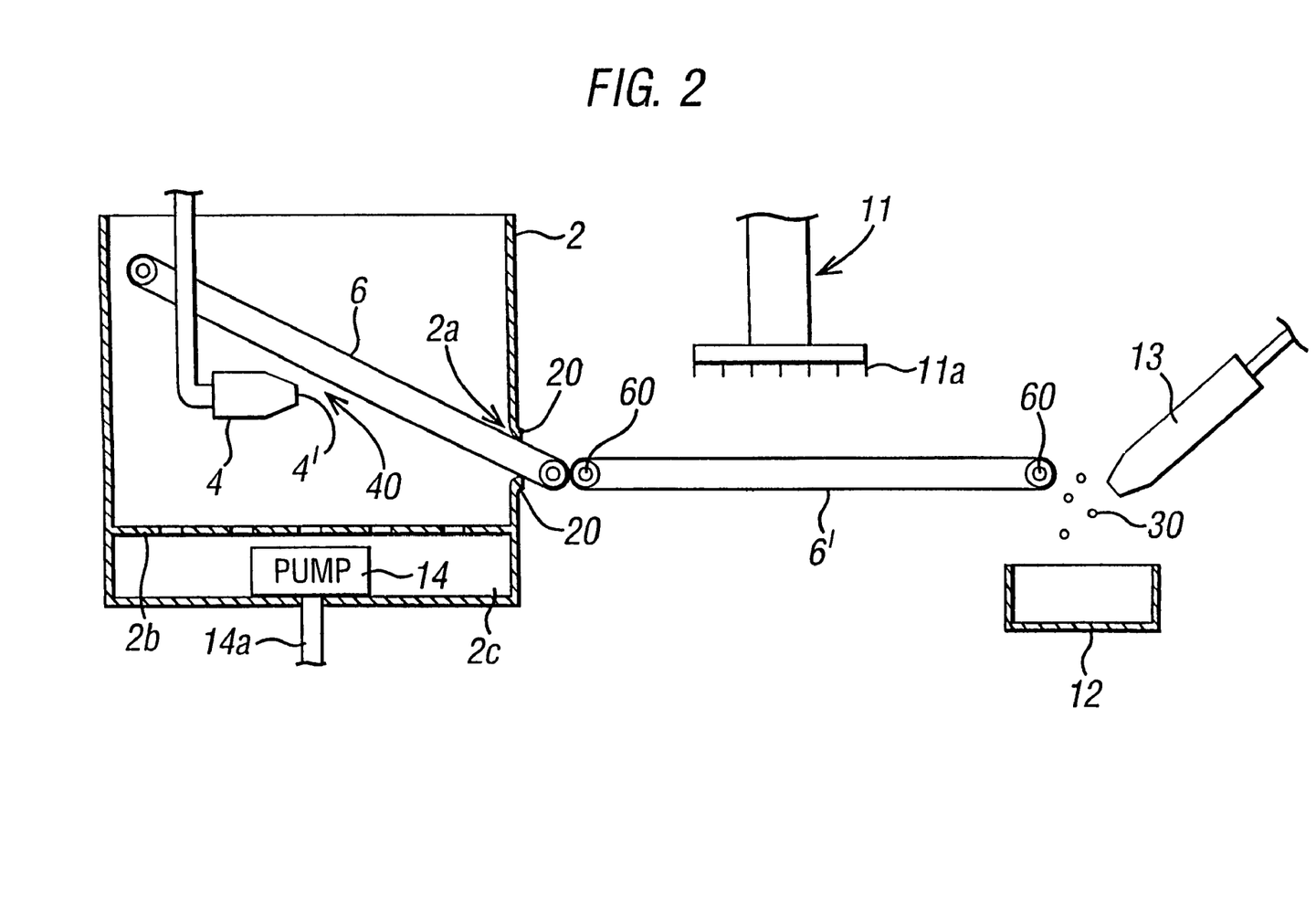
FIG. 2 shows a part sectional view taken along the line II-II in FIG. 1.

The support surface 6 is in the form of a conveyor belt supported along its length (see FIG. 2) by rollers 60 rotably mounted to supports (not shown) such that, as shown most clearly by FIG. 2, the conveyor belt 6 extends at an angle to the horizontal. One of the rollers 60 is fixedly mounted to the spindle 7a of a drive motor 7 mounted outside the chamber 2.

As shown in FIG. 2, the conveyor belt extends through an aperture 2a provided in the chamber 2. To maintain the environment within the chamber 2a and to assist in formation of the tablets as will be described below, the aperture 2a has flexible lips 20 formed of a rubber or plastics material which press onto the surface of the conveyor belt 6. An environmental control unit 8 may be mounted within the chamber so as to direct enable control of the temperature of the air in the region 40 where liquid issuing from the nozzle 4a is subject to the electric field established between the nozzle 4a and the support surface 6.

A perforate wall 2b of the chamber 2 separates the main chamber from a subsidiary chamber 2c which houses an exhaust pump 14. The exhaust pump 14 has an outlet 14a for exhausting air to the outside of the chamber 2.

A biologically acceptable carrier liquid is supplied to the tube 4 from a liquid supply reservoir 9 mounted outside the chamber 2 by means of a pump 10. The temperature of the reservoir 9 may be controlled so that its contents are thermally adjusted to produce fibres when sprayed. For example a solid may be heated to a liquid state ("melt") to be sprayed, or an inviscid liquid may be cooled to make it more viscous. In this way the range of products and formulations that can be sprayed may be extended beyond liquids that are sprayable at room temperature and may avoid the need for solvents.

As shown in FIG. 2 a horizontal further conveyor belt 6' is supported on rollers 60 adjacent the conveyor belt 6 so that in known manner material can pass directly from the conveyor belt 6 to the conveyor belt 6'. A cutting device 11 is mounted above the further conveyor belt 6' outside of the chamber 2 so that a matrix of cutting blades 11a of the cutting device are moveable towards and away from the conveyor belt. A hopper 12 is mounted beneath the end of the conveyor belt to receive the resulting tablets or pills.

As shown in FIG. 2, a spraying device 13 may be provided at the end of the further conveyor belt to spray the resulting tablets with a final coating as will be explained below.

In use of the apparatus shown in FIG. 1, the high voltage 5 is first switched on to establish an electric field between the nozzle 4' and the support surface 6. Typically, the high voltage applied to the support surface or spindle 6 will be approximately 20 kilovolts. Applying the high voltage to the support surface 6 and earthing the nozzle 4' acts to focus the electric field and produce less erratic spraying than would sometimes be produced if the high voltage was applied to the nozzle 4' and the surface 6 was earthed. The drive motor 7 and pump 14 are then activated so as to rotate or drive the conveyor belt 6'.

If required, as environmental control unit 8 may be used to adjust the ambient temperature so that either warm or cold air, dried or humidified flows through the chamber 2. The temperature of the air within the chamber 2 will be controlled to be appropriate for the formulation being sprayed. For example, the temperature may be controlled to have a value between 0° C. and 200° C., depending on the formulation being sprayed. The temperature may, depending upon the formulation being sprayed, be in the range of 30° C. to 200° C. or 50° C. to 100° C.

The liquid pump 10 is then activated to pump liquid to the tube at a rate of between 1 and 20 ml, for example about 4 ml (milliliters), per hour.

Liquid issuing from the output nozzle 4' forms, under the influence of the applied electric field, a Taylor cone and jet which solidifies to form a fibre which is attracted to and deposits on the support surface 6 as a fibrous web or mat. The speed of movement of the conveyor belt 6 is typically less than 1 meter/second ($ms^{-1}$). A conveyor belt 1 meter wide moving at 5 mm/s or 0.005 m/s should enable 100,000 tablets with a surface area of 2 $cm^2$ to be produced per hour.

The mat or web is moved away from the area of the high electric field by the conveyor belt, is squeezed slightly against the conveyor belt 6 by the resilient lips 20 which act to compress the fibre mat or web slightly and then transferred to the further conveyor belt 6'.

The cutting device 11 is reciprocated towards and away from the further conveyor belt 6' by conventional reciprocating means (not shown) in synchronism with the movement of the belt so that the cutting blades 11a of the cutting device cut the compressed mat or web into tablets or pills 30. Although not shown, a printing stage may be provided for printing information such as a logo or dosage amount on the tablets. The tablets or pills 30 then drop off the end of the further conveyor belt 6' and are collected in the hopper 12.

As noted above, a spraying device 13 may be provided to coat the individual tablets or pill's 30 with, for example, a sugar coating. The spraying device 13 may be a conventional spraying device or may be an electrohydrodynamic spraying device of the same type as the comminution arrangement 3.

Typically the gap between the outlet nozzle 4 and the support surface 6 is about 1 to 20 cm.

The use of the conveyor belt arrangement enables a continuous process and also allows the highly charged fibre web or mat to be moved away from the area of the electric field leaving a more appealing lower charged surface behind to facilitate the deposition of further material. In the arrangement described above, the nozzle 4' is arranged to spray horizontally onto the conveyor belt 6 which is arranged at an angle to the horizontal. This has the advantage that any undesired large or satellite droplets issuing from the nozzle 4' will, due to the influence of gravity, fall away from both the nozzle 4' and the conveyor belt 6. Where the possibility of satellite droplets is small and does not present a problem then the conveyor belt 6 may extend horizontally and the nozzle 4' may be arranged above or below the conveyor belt 6 so as to spray directly downwardly or upwardly, respectively, onto the conveyor belt 6.

The liquid supplied to the tube 4 may contain a pharmacologically or biologically active ingredient such as a drug or medicament to be imbibed by the patient, especially drugs acting upon the central nervous system where buccal delivery via the mouth mucosa will have specific benefits and/or where entry into the body via the gastro-intestinal tract is to be minimised for physiological reasons, for example to inhibit adverse side effects. Examples of such drugs are eletriptan and sildenafil.

As an example, the biologically acceptable carrier may be gelatin. Experiments to determine the optimum gelatin-based formulation for achieving a tablet which will maintain its shape but will dissolve or disintegrate readily on the tongue were carried out. These experiments were carried out using an annular nozzle which, for convenience, was arranged to spray onto a slowly rotating (for example 1 revolution/hour) 350 mm diameter metal plate rather than onto the conveyor belt 6. The nozzle 4' was separated from the plate by a distance which was varied between 60 and 200 mm and a voltage of between 25 and 30 kV was applied to the plate. Generally 30 kV was applied to the plate. The liquid to be sprayed to produce the desired tablets was supplied to the nozzle 4' with a flow rate between 10 and 20 ml per hour.

In this case, the liquid to be sprayed consisted of CRODA spray dried fish gelatin with the solvent being a water-ethanol mix. In the experiments, formulations were investigated in which 5 g of the fish gelatin was dissolved in between 17 and 30 ml of the water-ethanol solvent.

It was found that the spray performance of the formulation was affected by the overall ratio of water to ethanol content and also by the overall viscosity of the solution. The ratio of water to ethanol was varied between 2:1 and 1:2. It was found that a higher ethanol content produces a more sprayable solution but that an excess of ethanol causes the gelatin to precipitate out of solution with it being impossible to properly dissolve the 5 g of gelatin in an 8 ml water:12 ml ethanol (2:3) solvent mix. It was also found that a high proportion of water provides a more stable solution that is more difficult to spray and also produces a slightly wetter product that is more likely to contain droplets in addition to the desired fibre. The best formulations were found to have a solvent consisting of 7 to 9 ml of water and 10 to 11 ml of ethanol. The current preferred formulation is 8 ml of water, 10 ml of ethanol, 1 ml of peppermint flavouring (which is a mixture of water and isopropanol plus the flavouring) and 5 g of the spray dried fish gelatin.

The less viscous solutions (that is where there was 22 to 30 ml of solvent per 5 g of fish gelatin) sprayed in a more stable fashion but tended to produce droplets and some beaded fibres. In contrast, more viscous solutions having 17 to 21 ml of the solvent produced the desired distinct fibres and resulted in tablets having only a little friability.

Increasing the distance between the nozzle 4' and the support surface onto which spraying was being effected increased the likelihood of fibre formation (because it allowed further time for evaporation of the solvent) and made the resultant tablet more fibrous and friable. In contrast, placing the nozzle 4' very close (60 to 70 mm) to the support surface had the opposite effect with the solvent having less chance to evaporate and thus encouraging a less friable but more dense product. As a result of these experiments, it was found that the optimum distance for spraying the current preferred formulation to achieve the desired low density low friability tablets was a separation of between 100 and 200 mm between the nozzle 4' and the plate with the actual distance within this range being fairly flexible.

The addition of sweeteners to increase the palatability of the tablet was investigated. It was found that the addition of a little (50 mg or so) of saccharine to the liquid resulted in no noticeable effect on the end tablet apart from the desired sweetness. Surprisingly, however, when a similar quantity of d-sorbitol (mannitol) was added, it was found that the tablets shrank catastrophically over a day or, so resulting in a high density rubber-like structure which would not dissolve readily in the mouth or on the tongue.

Other grades of gelatin may be used to adjust the physical properties of the product. For instance, a product made purely from fish gelatin dissolves extremely quickly in water but can also be dissolved by sweat on the fingers. Although this problem can be countered by a thin coating applied to the finished pill or tablets, other less soluble gelatine grades may be used instead of, or as well, as the fish gelatin to make it more robust and less fryable. Also the degree of spray drying of the gelatin may affect the characteristics of the end product.

Further experiments have shown that many other formulations may be used which do not contain animal products and are therefor suitable for vegetarians. These will include alternative solutes such as polyvinyl pyridine, polyvinyl alcohol, poly-sucrose, other poly-saccharides, such as starch and cellulose and its derivatives, sugars and confectionery mixtures, such as toffee and caramel, and other biologically compatible products that can be formulated into a liquid solution or made liquid through the application of heat and which will dissolve or melt on contact with wet surfaces as required. Mixtures of different polymers may also be used, for example a small quantity of another biologically acceptable polymer may be added to a gelatin formulation to improve its performance.

The following table gives specific examples of polymer formulations that may be used as the biologically acceptable carrier. In this table the flow rate column indicates the flow rate from the outlet of the supply tube, the voltage indicates the voltage difference between the outlet tube and the conveyor belt used to cause electrohydrodynamic spraying and the comments column indicates the spray properties and characteristics of the resulting web or mat product. The separation is the distance of the supply tube outlet from the conveyor belt and "Mw" is the molecular weight.

| Polymer | Formulation | Flow Rate | Voltage (kV) | Separation (at room temperature) | Comments |
|---------|-------------|-----------|--------------|----------------------------------|----------|
| "Luviskol" a vinyl-pyrolidone/vinylacetate copolymer Manufactured by BASF, 67056 Ludwigshafen Germany | Luviskol is provided as a 50% solid in ethanol solution. This in turn is diluted with extra ethanol in a ratio of two parts of Luviskol to one part of ethanol | upto 30 ml/hr | 15 kV | Wide range from 5 cm to 15 cm | Very stable spray. Build up fairly rapid. Product very soluble. Large fibres. |
| Polyvinyl-pyrolidone | Mw 360,000: 0.5 g in 10 ml ethanol | upto 20 ml/hr | 15-20 kV | Wide range from 5 cm to 15 cm | Very stable. Not a very rapid build up of product |
| Gelatin | 5 g in: 8 ml water, 12 ml ethanol | upto 30 ml/hr | 20-30 kV | Wide range from 5 cm to 15 cm | Not very stable. However rapid build up of web. Product is very soluble in water |
| Polyvinyl-alcohol | Mw 100,000 and 130,000. Concentration of 0.1 g/ml | 10 ml/hr | 14-20 kV | 6 to 10 cm | Very stable, very soluble in water. Lower molecular weights produce |

-continued

| Polymer | Formulation | Flow Rate | Voltage (kV) | Separation (at room temperature) | Comments |
|---|---|---|---|---|---|
| | in 1:1 water and ethanol | | | | denser product, which is less soluble, and higher molecular weights are too viscous. |
| "Luvitec VPI 55" vinyl-pyrolidone/ vinyl-imidazole copolymer Manufactured by BASF | ~4 g in 10 ml ethanol | 5 ml/hr | 12 kV | 9 cm | Multi-jets, very soluble loosely packed mat. Very tacky. Stable. Possible to make more concentrated. |

Figure 3:
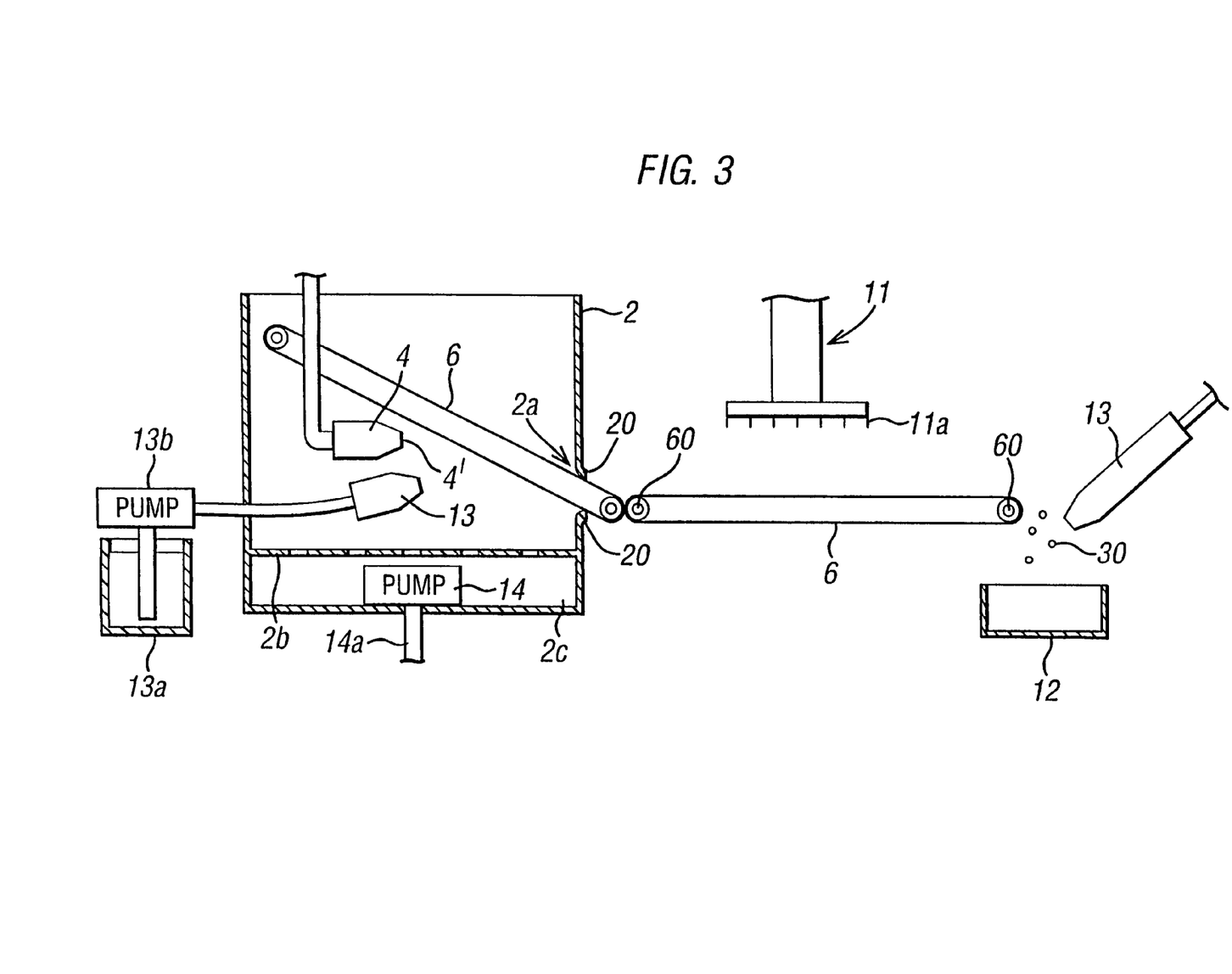
FIG. 3 shows a very schematic part sectional view of a modified form of the apparatus shown in FIG. 1.

FIG. 3 is a view similar to FIG. 2 showing a modification of the arrangement shown in FIG. 2. As can be seen from FIG. 3, the apparatus 1a shown in FIG. 3 differs from that shown in FIGS. 1 and 2 in that the sprayer 13 is provided within the chamber 2 and is arranged so as to direct a spray at liquid issuing from the nozzle 4a so that the fibre is coated as it is formed. FIG. 3 also shows a spraying liquid reservoir 13a and pump 13b.

In the embodiments described above, the tablets or pills are formed using the cutting device 11. Different forms of cutting devices may, of course, be used. For example, a pair of reciprocating knives may be provided one on either side of the conveyor belt each arranged to cut at an angle to the length of the conveyor belt so as to produce lozenge shaped tablets or a rolling blade may be used. As another possibility, a cutter defining a plurality of tablet or pill shapes may be used which is lowered onto the fibrous mat to cut an area of the fibrous mat into an array of pill or tablet shapes. By applying suction to the cutting device, the cut shapes may then be lifted from the fibrous mat by the cutting device and transferred to and aligned with a blister pack base. Once the cutting device has been correctly positioned over the blister pack base, then the suction pressure may be reversed so as to blow the tablets gently into respective receptacles in the blister pack base. This cutting device may be arranged to cut out the pills or tablets so that they have a circular or oval shape. To minimise wastage, the cutting device may, alternatively, be arranged to cut out the tablets so that they have a rectangular or hexagonal shape with the corners of the rectangles or hexagons being rounded.

In the apparatus described above, the fibres are formed using a single cylindrical liquid supply tube 4 having an annular outlet nozzle 4'. However, the apparatus may be provided with an array of such liquid supply tubes extending transversely of the direction of movement of the conveyor belt 6 or even with a matrix of such liquid supply tubes. Where such an array is used, then the separate liquid supply tubes each provide a comminution site. In order to avoid interference effects between the separate comminution sites, the spray heads should be separated by a distance of at least 10 to 20 cm, or provided with electrostatic screening electrodes. Alternatively or additionally, a slot-like nozzle may be used.

Figure 4:
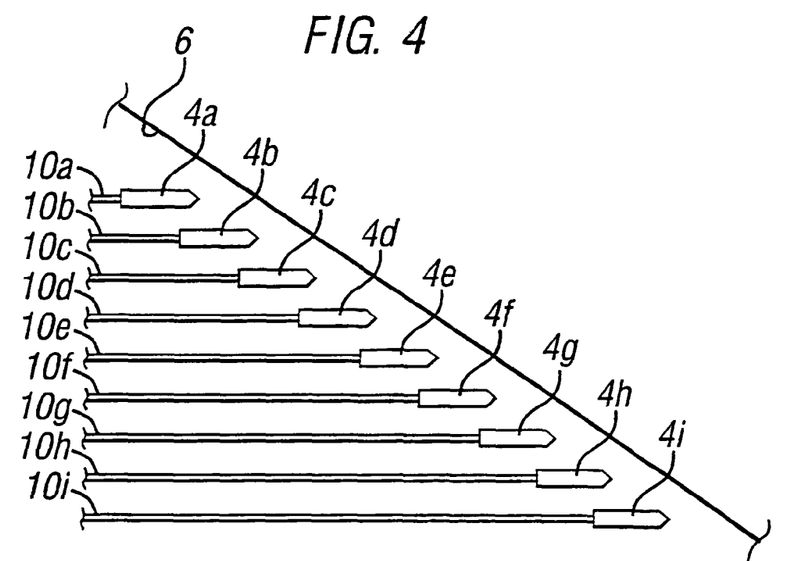
FIG. 4 shows very schematically a further modification of the apparatus shown in FIG. 1.

In addition, or as an alternative, a number of liquid supply tubes may be arranged along the length of the conveyor belt. Typically, the spacing between liquid supply tubes in this longitudinal direction should be 20 to 40 cm, for example 30 cm, although they may be placed closer together if the individual liquid supply tubes are electrostatically screened. FIG. 4 illustrates very diagrammatically a modification of the apparatus shown in FIGS. 1 and 2 wherein nine liquid supply tubes 4a to 4i are arranged so as to extend along the length of the conveyor belt 6. As shown in FIG. 4, each liquid supply tube is connected to a respective liquid supply pipe 10a to 10i to which liquid is pumped via a corresponding pump (not shown) from a corresponding reservoir (not shown). Thus, each of the liquid supply tubes 4a to 4i will be coupled via a liquid supply pipe and pump to a reservoir in the manner similar to that shown in FIG. 1 for the liquid supply tube 4.

Providing a plurality of liquid supply tubes along the length of the conveyer belt has a number of advantages. In particular, it enables different liquids to be supplied via the different liquid supply tubes 4a to 4i. As one example, alternate liquid supply tubes 4a, 4c, 4e and 4g may supply the polymer liquid formulation discussed above while the intervening liquid supply tubes 4b, 4d, 4f and 4h may supply a tacky ingredient such as gum arabic or gum tragacanth to facilitate adhesion of the fibres to one another and the final liquid supply tube 4i may supply a flavouring or sugar coating. Also, the use of a plurality of nozzles supplying different liquids enables, for example, active ingredients which are lyophilic as opposed to hydrophilic to be incorporated into the tablets.

To further facilitate adhesion of the fibres to one another and to make the resulting product less fluffy, if required, the nozzles of alternate liquid supply tubes may be charged to opposite polarities. In addition, one or more of the liquid supply tubes 4a to 4i may be replaced by a spraying device which sprays charged dry powder of the opposite polarity to the fibres so that the dry powder is attracted to and sticks to the fibre. Such a dry powder may contain an active ingredient or ingredients for the tablet and/or flavourings or colorings. One advantageous way of producing such electrically charged dry powder would be to use the triboelectric charging process. Another way would be to use ionic bombardment. Both these techniques are well known. The ionic bombardment process provides a copious supply of ions which are attracted directly to the fibres and may be desirable in order to reduce the charge on the sprayed mat.

Typically, it is possible to achieve charge of the order of 1 coulomb per kilogram when producing the fibres from liquid but charge of only the order of $10^{-3}$ coulombs per kilogram for dry powder. Thus, if the dry powder is produced to be of the opposite polarity from the fibres, then the overall mat before separation into the tablets will still be charged to the polarity of the fibres but will have an overall reduced charge. This enables a large amount of oppositely charged particles to be applied to the spray mat.

In an embodiment, the liquid supply tubes arranged along the length of the conveyor belt may be arranged so as to provide, alternately, a supply of fibres and a supply of an active ingredient with opposite plurality voltages being applied to longitudinally adjacent liquid supply tubes so that a layer of fibres of one polarity is deposited followed by a layer of active ingredient of the opposite polarity followed by a layer of fibres of the one polarity followed by a layer of active ingredient of the other polarity and so on to the desired thickness. Different active ingredients may be provided in the different active ingredient layers and different fibres or fibre thicknesses may be provided in the different fibre layers. This may allow, for example, a multiple therapy tablet to be produced which enables, for example, rapid buccal delivery of one active ingredient and slower delivery via the gastro intestinal tract of the same or a different active ingredient.

As described above, an environmental control unit may be provided to control temperature and/or humidity. Where a plurality of liquid supply tubes spaced apart along the length of the conveyor belt are provided then each liquid supply tube may be provided with its own local environmental control unit which may be provided, for example, immediately downstream of the liquid supply tube to allow, for example, for drying of the just-formed layer prior to deposition of further material on that layer.

Another way of electrically compacting the product is to apply alternating polarities to the spray nozzles over time. The frequency would typically be quite low so the electrohydrodynamic process has time to adjust. Frequencies below 10 Hz are preferable.

Figure 5:
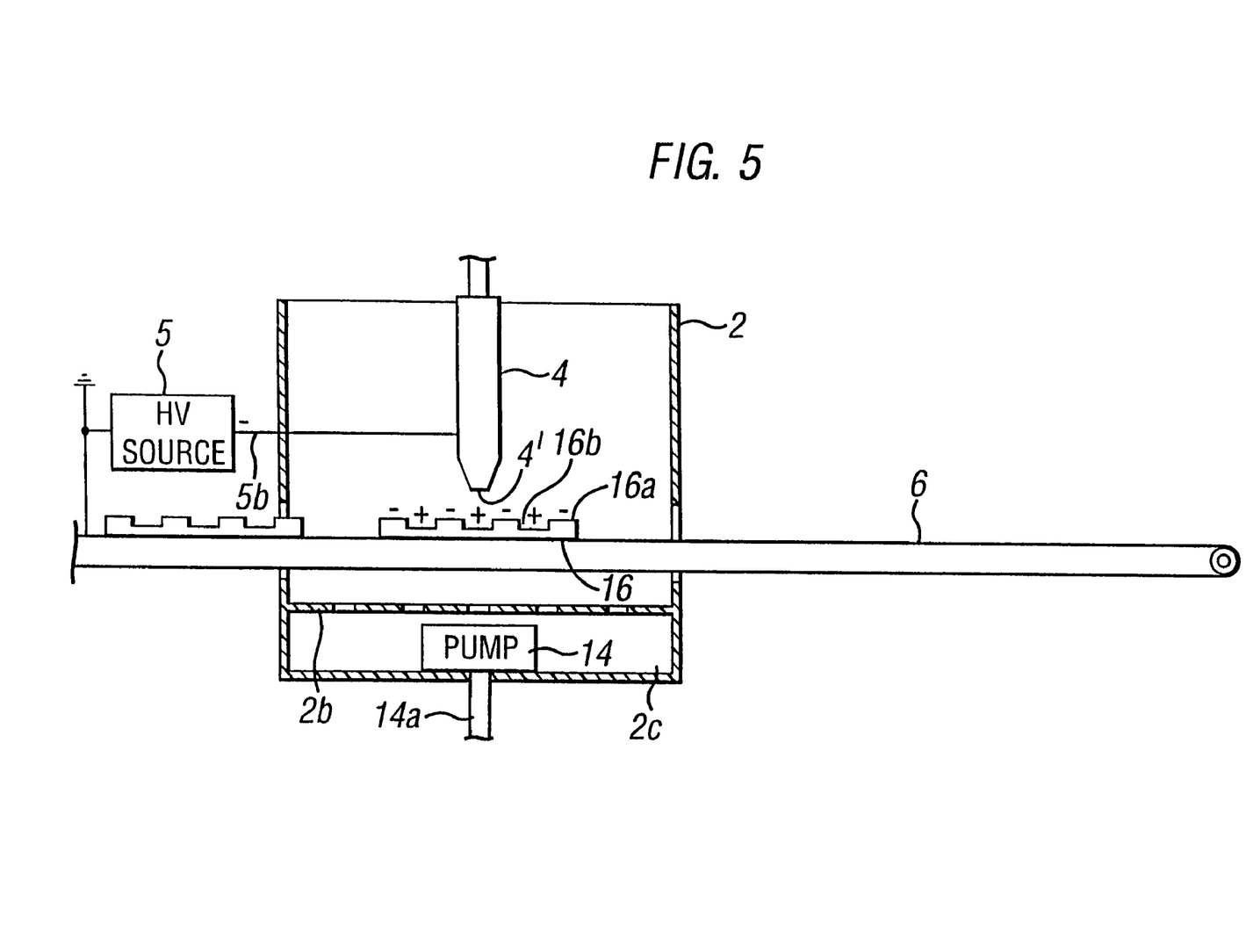
FIG. 5 shows a part sectional very diagrammatic view of a further modification of the apparatus.

FIG. 5 illustrates very diagrammatically a further modification of the apparatus described above. In this example, the conveyor belt 6 is horizontally arranged, but the further conveyor belt 6' and the cutting device 11 are omitted and a field controlling arrangement is provided so as to direct the fibres only towards certain areas of the surface 6. As shown, this is achieved by provided on the surface of the conveyor belt 6 a tray-like arrangement 16 having a regular array of tablet or pill sized and shaped recesses 16. The tray-like arrangement is designed so that the interior surface of each recess 16b is positively charged while the islands 16a between the recesses are negatively charged.

In this arrangement, the nozzle 4' is arranged to be negatively charged and the belt earthed by the high voltage source 5 so that the material issuing from the nozzle is negatively charged and thus will be attracted into the recesses 16b but repelled from the islands 16a so that a series of individual tablet sized mats or webs of fibres are produced. Where non-gelatinous products are used the spray distance can be much reduced to around 1 to 2 cm, and in such cases the nozzle can be placed just above, making it easier to direct the spray into the well.

Figure 6:
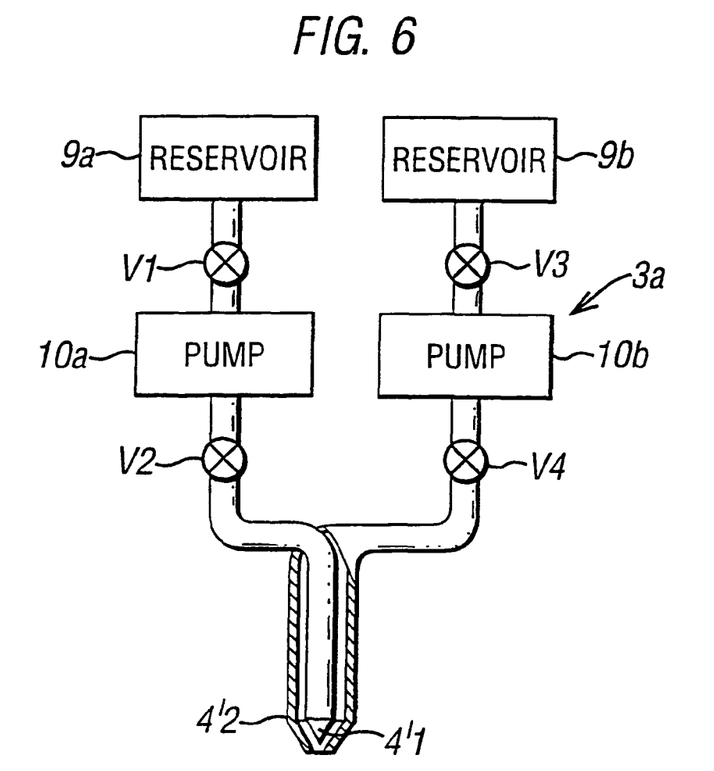
FIG. 6 shows diagrammatically a modified form of comminution arrangement for use in the apparatus shown in any of FIGS. 1 to 5.

FIG. 6 illustrates that schematically a further modification which may be made to the comminution arrangement 3. The arrangement 3a shown in FIG. 6 has two reservoirs 9a and 9b containing different liquids each coupled by a respective valve V1 and V3, a respective pump 10a and 10b and a further valve DV and V4 to a respective outlet nozzle 4'1 and 4'2. This arrangement enables a first liquid to be provided within a curtain of the second liquid enabling a cord or coated fibre to be produced. It would be appreciated that FIG. 6 is only very schematic. Further details of an arrangement for enabling a first liquid to be supplied within a second liquid are described in WO 98/03267 (see especially FIGS. 11 and 14) the whole contents of which are hereby incorporated by reference.

Figure 7:
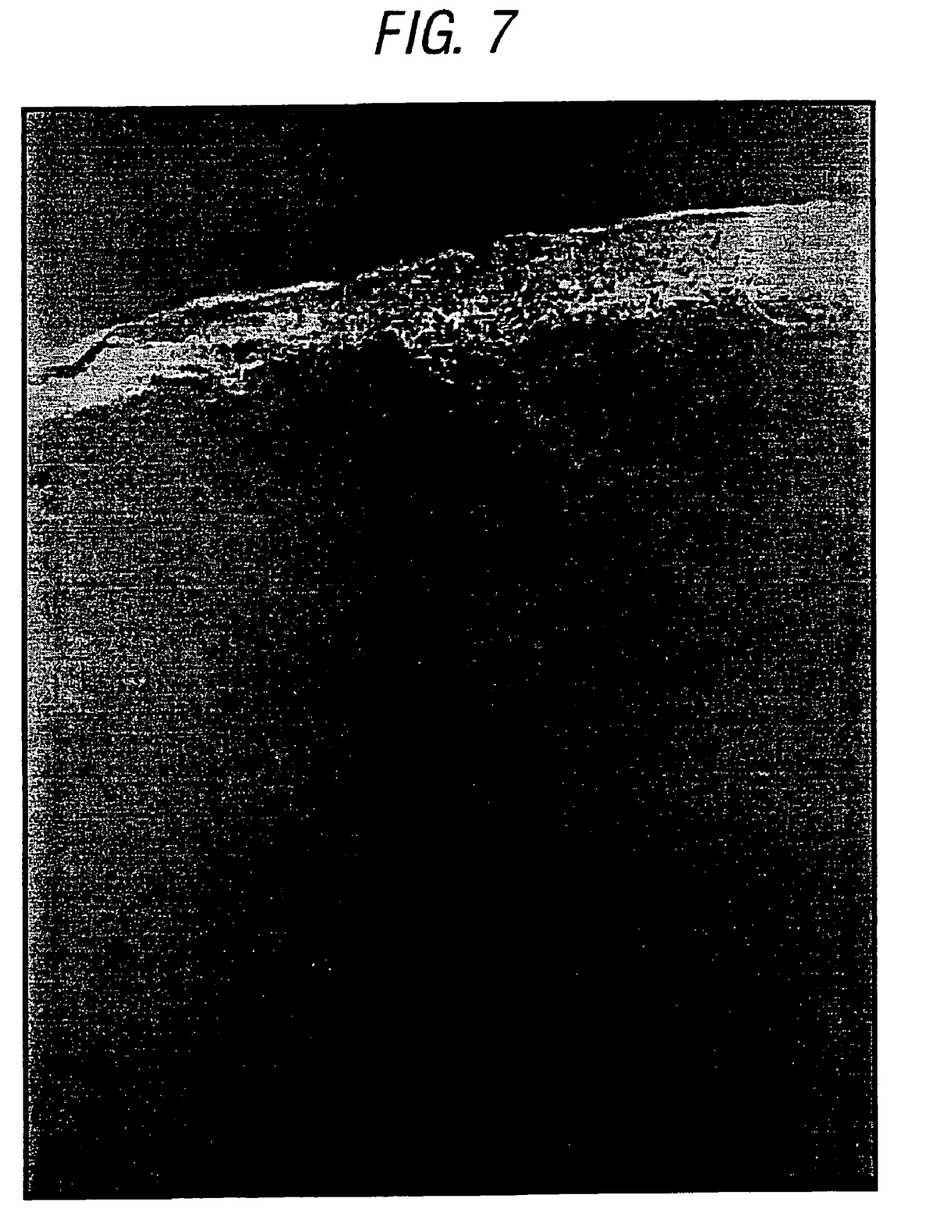
FIGS. 7 to 9 show electronmicrographs with FIGS. 7 and 8 illustrating the structure of a tablet produced by the conventional freeze gelling technique and FIG. 9 illustrating the structure of a tablet produced using a method embodying the present invention.
Figure 8:
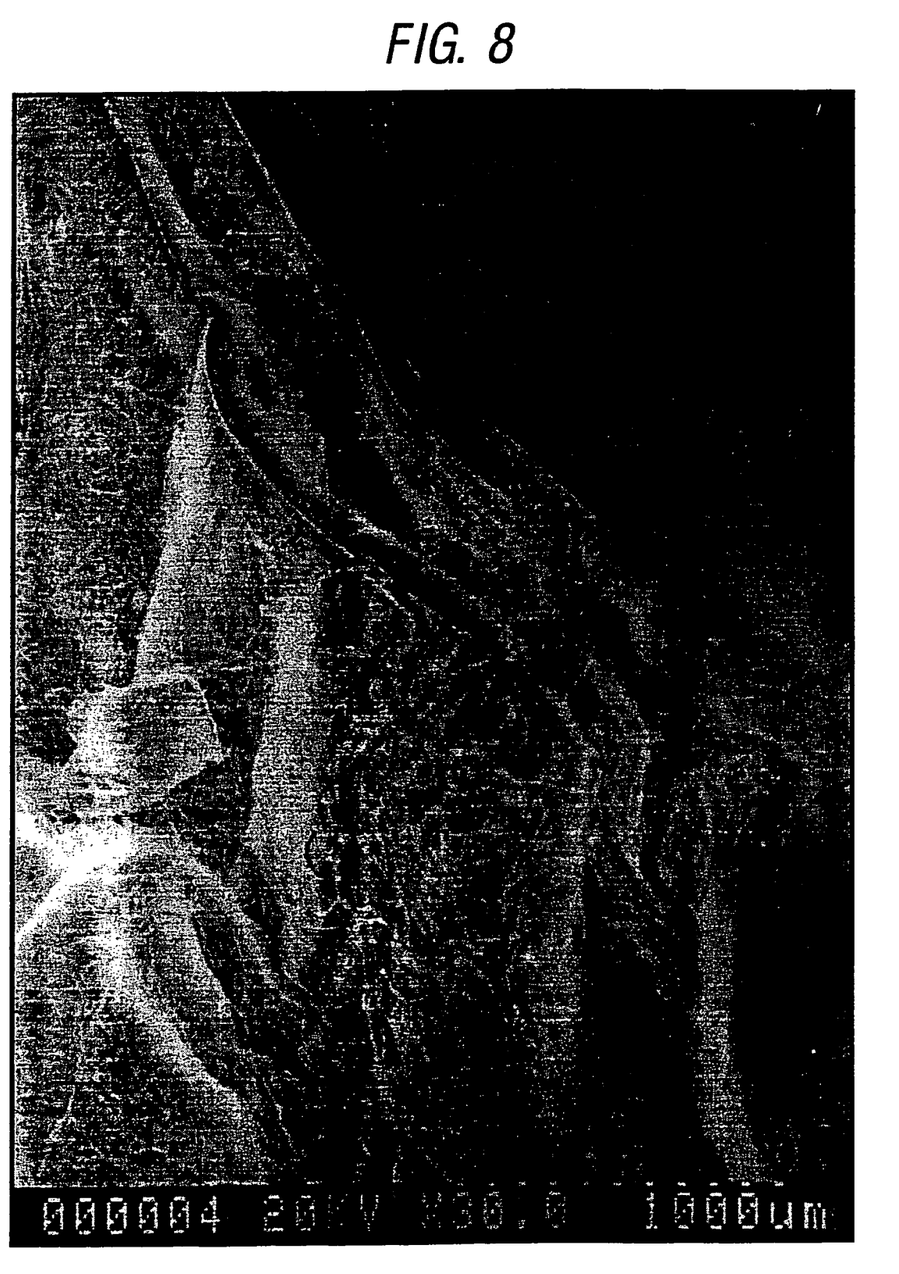
Figure 9:
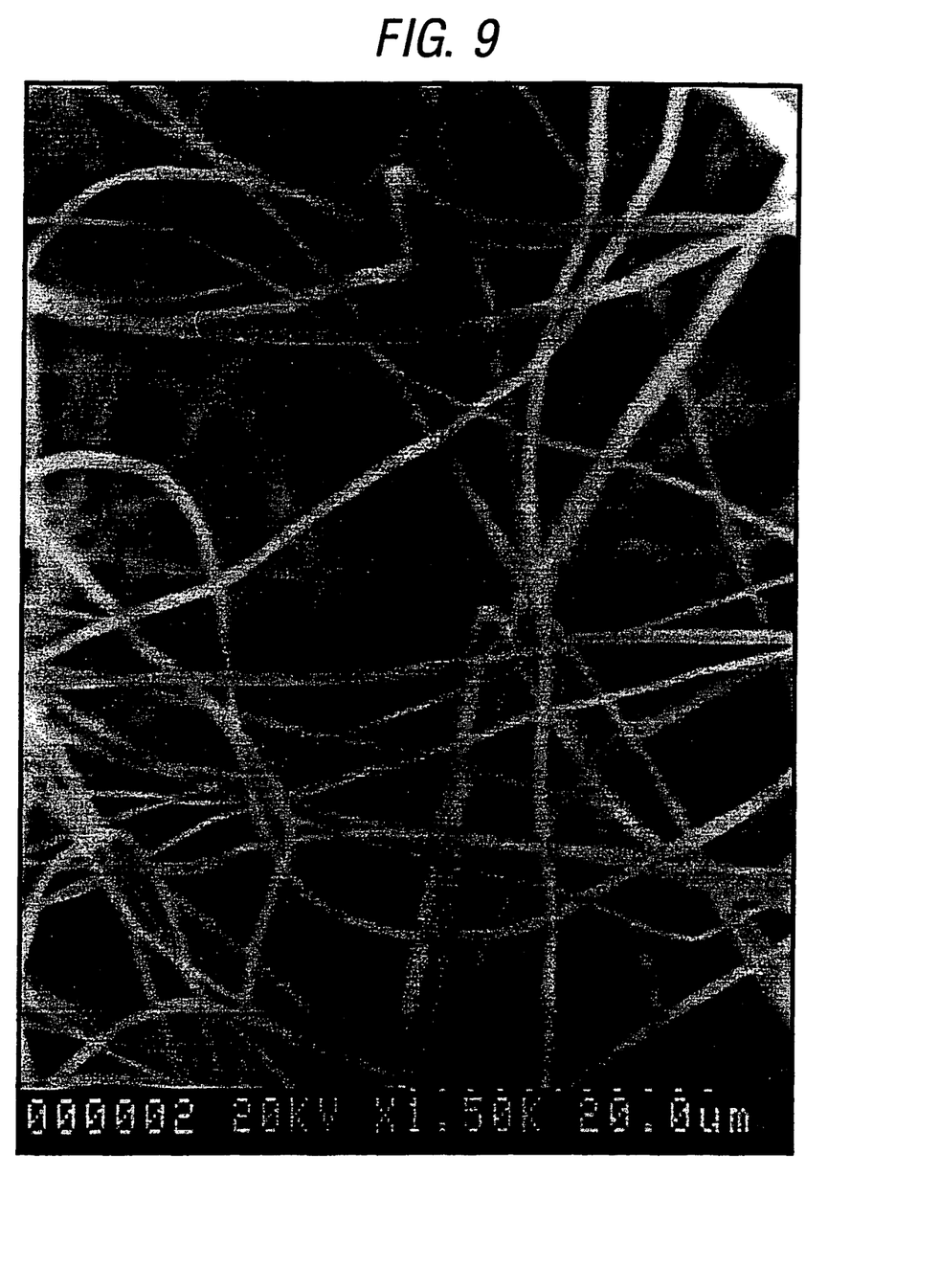

FIGS. 7 to 9 are electronmicrographs showing in FIGS. 7 and 8 the structure of a conventional freeze dried tablet and in FIG. 9 the mat or web like fibre structure of a tablet produced using the apparatus shown in FIGS. 1 and 2 and the gelatin solution mentioned above. As can be seen, the resulting fibre consists of a fine mat or web of strains or fibres which appear to be simply individual strands of rapidly dried polypeptide chains that have become entangled to form strands or fibrils. These in turn would appear to have become entangled with one another forming strings which themselves become intertwined to form rope like structures which overlay one another to form a fibrous cotton wool like material. This very open fibre structure can be fully hydrolysed in the mouth with full breakdown of the secondary structure so that the fibres become disentangled but will not form junctions zones which would result in gelling of the product which would be undesirable.

The active ingredient or ingredients to be supplied by consumption of a tablet or pill produced using the apparatus described above may be any agent or substance which provides a desired effect in the consumer. For example, the active ingredient may be a medicament for use in the treatment by way of therapy, surgery or diagnosis or otherwise to improve quality of life of a human being or other animals. For example, the active ingredient may be nicotine, morphine, a vitamin, an antiseptic, an anti-inflammatory, an antibiotic, an anti-cancer agent or other pharmaceutical product, a vaccine, a protein, or an enzyme.

The present invention also has applications outside the medical field. Thus, the apparatus described above may be used to produce confectionary products which melt in the mouth. In such cases, the active ingredients may comprise at least one or more of the following: a flavouring; chocolate; a colorant; and a sweetener.

The fibres may be formed using any suitable biologically acceptable or compatible polymer that is hydrophilic so that, on contact with a wet surface, it effectively deliquesces becoming liquid by absorbing the water, thereby dissolving. Suitable such polymers include food grade gelatins, polyvinyl pyridine, polyvinyl alcohol, polysucrose, other polysaccharides such as starch and cellulose and its derivatives, sugars and confectionary mixtures such as toffee and caramel and any other biologically compatible products that can be formulated into a liquid solution suitable for use in the electrohydrodynamic comminution process or can be made liquid to the application of heat.

As used herein the term "biodissolvable" means capable of being dissolved or disintegrated in the mouth or on the tongue of a human being or other animal and on another wet surface such as an open wound where the pad or tablet would dissolve quickly to release a drug or other product onto the surface of the wound or an eye ball surface to deliver for example, a local anaesthetic to the eye ball after surgery. Tablets manufactured by a method in accordance with the invention may also be provided so as to be reconstituted in water for injection or drinking or eating with food for example.

Other modifications will be apparent to the skilled person in the art.

The invention claimed is:

1. A method of manufacturing a rapid dissolving tablet suitable for buccal delivery of an active agent containing one or more active medicaments, comprising the steps of
   (1) supplying a biologically acceptable carrier liquid through a first supply tube to an outlet of said first supply tube, said biologically acceptable carrier liquid comprising a solution of a biologically acceptable polymer;
      (a) wherein said biologically acceptable polymer is selected from the group consisting of gelatin, polyvinyl pyrrolidone, vinylpyrrolidone/vinylacetate copolymer, vinylpyrrolidone/vinylimidazole copolymer, and polyvinyl alcohol in a mixture of water and ethanol; and
      (b) wherein said water and ethanol are present in said carrier liquid at a ratio of from about 1:0.8 to about 1:1.5;
   (2) establishing an electric field between the outlet of said first supply tube and a support surface that is spaced from the outlet to cause liquid issuing from the outlet to form at least one fiber or fibrils of said carrier liquid;
   (3) causing said fibers or fibrils to deposit onto the support surface to form a fibrous porous web or mat;
   (4) supplying a biologically acceptable carrier liquid comprising an active medicament through a second supply tube to an outlet of said second supply tube;

(5) applying a charge to said carrier liquid of Step 4 opposite the charge of said first electric field of Step 2 to form a layer of fibers or fibrils comprising said active ingredient on top of said fibrous porous web or mat from Step 3;

(6) repeating Steps 1-3 so as to deposit a layer of fibers or fibrils on the surface of the layer of fibers or fibrils of active ingredient from Step 5; and (7) forming a plurality of individual tablets from the layers produced from step 6; and wherein the individual tablets are capable of rapid dissolution suitable for buccal delivery.

2. The method according to claim 1, wherein said carrier liquid consists essentially of a hydrophilic solution of gelatin dissolved in a mixture of water and ethanol, wherein a sweetener is incorporated into said fibers.

3. The method according to claim 2, wherein the sweetener is saccharine.

4. The method according to claim 1 wherein said biologically acceptable polymer is polyvinyl alcohol having a molecular weight of 100,000 to 130,000.

5. The method according to claim 1 wherein said biologically acceptable polymer is gelatin.

6. The method according to claim 1 wherein said biologically acceptable polymer is polyvinyl pyrrolidone.

7. The method according to claim 1 wherein said active ingredient is a confectionary material.

8. The method according to claim 1 wherein said active ingredient is a medicament for a human or an animal.

9. The method according to claim 8 wherein said active ingredient is a medicament for an animal.

10. The method according to claim 8 wherein said active ingredient is a medicament for a human.

11. The method according to claim 8 wherein said active ingredient is a medicament selected from the group consisting of a drug, vaccine, enzyme or diagnostic agent.

* * * * *